United States Patent
Sabbi

(10) Patent No.: US 12,390,373 B2
(45) Date of Patent: Aug. 19, 2025

(54) MACHINE AND A METHOD FOR MANUFACTURING SANITARY PRODUCTS

(71) Applicant: Fameccanica.Data S.p.A., San Giovanni Teatino (IT)

(72) Inventor: Piero Sabbi, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 413 days.

(21) Appl. No.: 17/845,304

(22) Filed: Jun. 21, 2022

(65) Prior Publication Data

US 2022/0409439 A1 Dec. 29, 2022

(30) Foreign Application Priority Data

Jun. 24, 2021 (EP) ...................................... 21181348

(51) Int. Cl.
*A61F 13/15* (2006.01)

(52) U.S. Cl.
CPC .. *A61F 13/15723* (2013.01); *A61F 13/15747* (2013.01); *A61F 2013/15715* (2013.01); *A61F 2013/15821* (2013.01)

(58) Field of Classification Search
CPC .......... A61F 13/15723; A61F 13/15747; A61F 2013/15715; A61F 2013/15821; A61F 2013/49074; A61F 2013/53445; A61F 2013/5355; A61F 13/49058; A61F 13/15577; A61F 13/15707
See application file for complete search history.

(56) References Cited

U.S. PATENT DOCUMENTS

| | | | |
|---|---|---|---|
| 8,702,671 B2 | 4/2014 | Tsang et al. | |
| 2011/0130736 A1* | 6/2011 | Tsang | ................ A61F 13/49019 604/378 |
| 2016/0331597 A1* | 11/2016 | Piantoni | ............ A61F 13/15764 |
| 2021/0007879 A1 | 1/2021 | Woods et al. | |

FOREIGN PATENT DOCUMENTS

| | | |
|---|---|---|
| CN | 102695483 A | 9/2012 |
| CN | 203417296 U | 2/2014 |
| CN | 105208990 A | 12/2015 |
| CN | 106029026 A | 10/2016 |
| CN | 209203779 U | 8/2019 |
| EP | 3552591 A1 | 10/2019 |
| WO | 2011056205 A1 | 5/2011 |

OTHER PUBLICATIONS

European Search Report dated Dec. 8, 2021. 4 pages.
Chinese Office Action issued in counterpart Chinese application dated May 25, 2023.

* cited by examiner

*Primary Examiner* — Christopher W Raimund
(74) *Attorney, Agent, or Firm* — RMCK Law Group PLC

(57) ABSTRACT

A machine and a method for manufacturing sanitary product with an hourglass shaped absorbent core, such as a panty liner or a light-inco diaper. The machine and the method allow shaping of the core into an hourglass shape with minimized scrap.

12 Claims, 2 Drawing Sheets

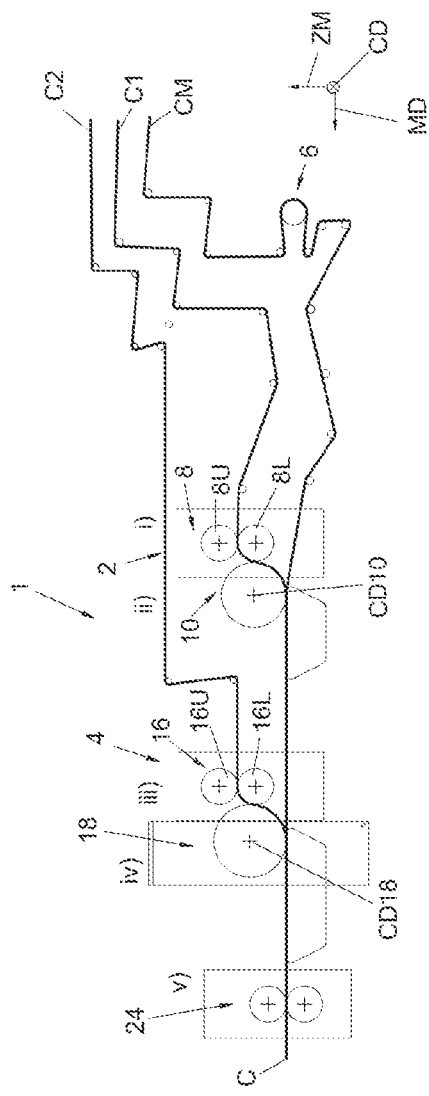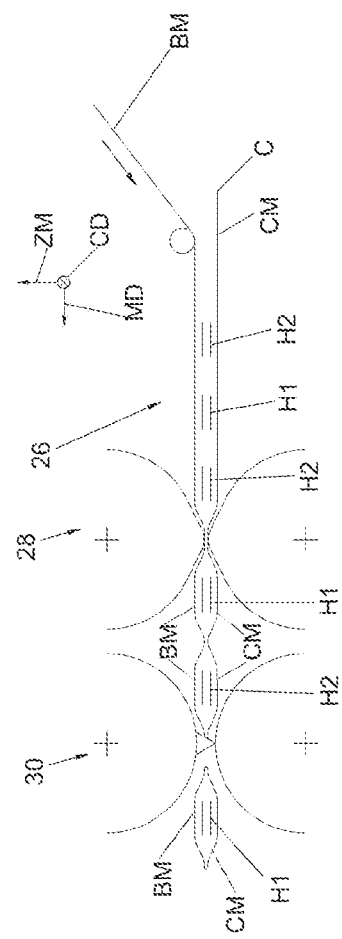
Fig.1
Fig.1A

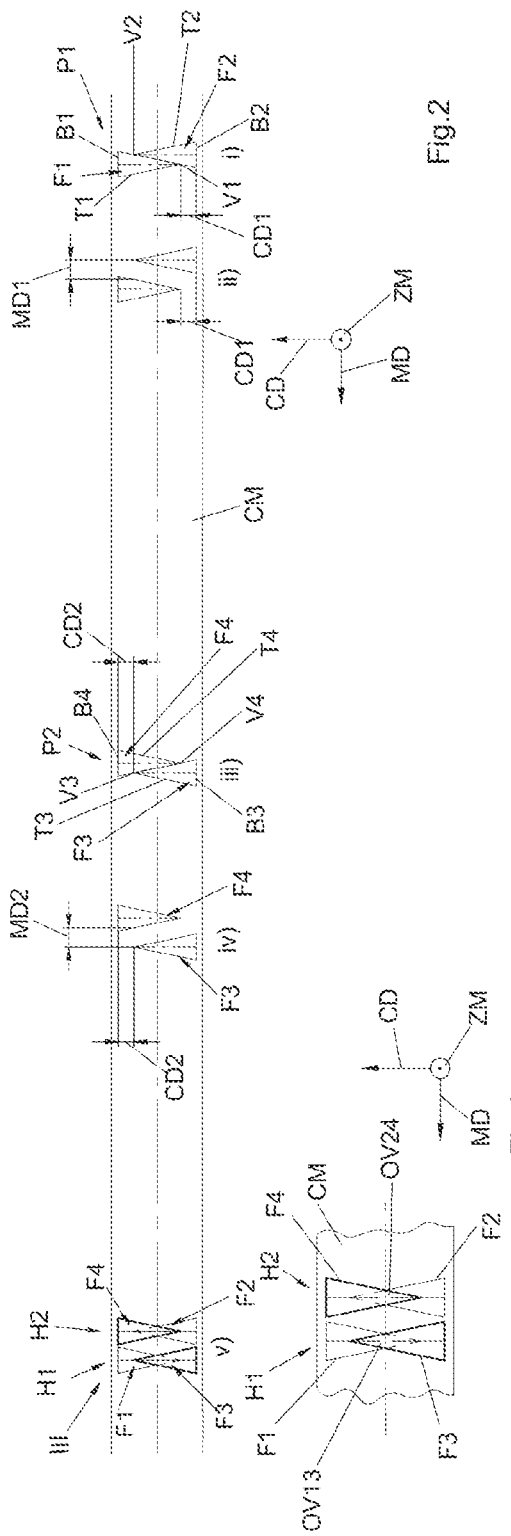
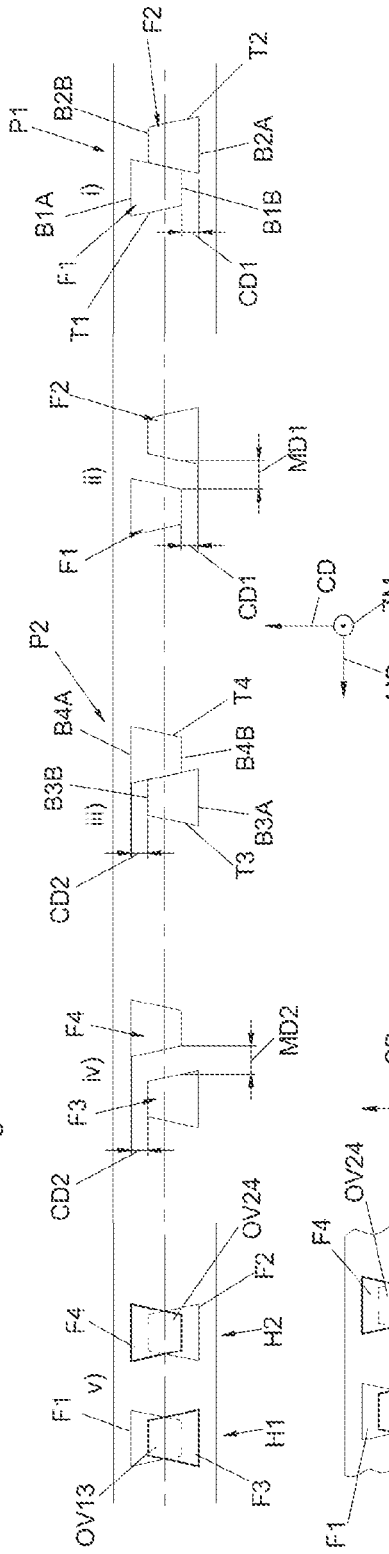

MACHINE AND A METHOD FOR MANUFACTURING SANITARY PRODUCTS

CROSS-REFERENCE TO RELATED APPLICATION

This application claims priority to European Patent Application No. 21181348.0 filed Jun. 24, 2021. The disclosure of the above application is incorporated herein by reference in its entirety.

FIELD OF THE INVENTION

The present invention relates to the manufacturing of sanitary products, particularly diapers or sanitary pads.

PRIOR ART

A variety of sanitary products such as diapers, sanitary pads or the like are known that feature a hourglass shaped outline with a multi-layer structure generally including a top sheet, a back sheet, and an absorbent core sandwiched between the top sheet and the back sheet.

The so-called panty liners, i.e. sanitary pads for late days of the menstrual flow, which are characterized by a lighter flow, or diapers known as "light inco" for light incontinent users are examples of such products.

A common problem with these products is the inherent amount of scrap, particularly of the high grade core materials (which may comprise SAP loaded materials, ADLs, or in any case raw materials that are the result of earlier processing stages which add value and costs to the same), during processing on account of the hourglass shape, which does not lend itself to the definition of cutting patterns on the webs they are made from which results in little or no scrap. In other words, the hourglass shape is inherently unsuitable to be assembled—in a modular fashion—into a pattern with fully shared boundaries between adjacent hourglass shaped figures, whereby at least part of the boundaries of adjacent hourglass shaped figures come to define scrap figures, i.e. portions of the web that get discarded when the final hourglass shapes are cut to shape out of the web.

This is clearly undesirable, as the discarded material is hardly recyclable in line, and accordingly is to be disposed with in a way that is environmentally compatible. As also noted, the discarding patches or cut outs of high grade core material is an inherent economic issue, as it is valuable "raw" material.

OBJECT OF THE INVENTION

The object of the present invention is to solve the above mentioned technical problems. More specifically, it is an object of the invention that of providing a machine and a method for manufacturing sanitary products, particularly hourglass shaped sanitary products such as panty liners or light-inco diapers, which results in an extremely low scrap manufacturing cycle.

SUMMARY OF THE INVENTION

The object of the invention is achieved by a machine and a method having the features of the claims that follow, which form an integral part of the technical disclosure provided herein in relation to the invention.

BRIEF DESCRIPTION OF THE FIGURES

Further features and advantages of the invention will become apparent from the following description with reference to the annexed figures, provided purely by way of non limiting example wherein:

FIG. 1 is a schematic view of a machine according to the invention,

FIG. 1A is a schematic view of an optional end station of the machine of FIG. 1, FIGS. 2, 4 are plan, schematic view of subsequent manufacturing steps that are carried out by a machine and a method according to the invention, and FIGS. 3, 5 are enlarged views corresponding to pointers III and V of FIGS. 2, 4 respectively.

DETAILED DESCRIPTION

Reference number 1 in FIG. 1 designates as a whole a machine for manufacturing sanitary products according to the invention.

The machine 1 comprises:
- a first processing unit 2 for a first core material C1, the first core material C1 comprising a first web material,
- a second processing unit 4 for a second core material C2, the second core material C2 comprising a second web material,
- a supply unit 6 for a carrier material CM, the carrier material CM comprising a third web material.

Each of the first, second, and third web materials (i.e. each of the core material C1, the core material C2 and the carrier material CM) can be stored as a coil/bobbin, a pleated stack (fold and stack), or can be formed in line, whereby either upstream of the machine 1 or in the machine 1 itself a forming apparatus is provided that outputs the required web material to the machine 1.

The carrier material CM is generally a nonwoven web material commonly used in the manufacturing of sanitary products. As will emerge from the description that follows, the carrier material CM which comprises the third web material is a top sheet of the sanitary product.

As to the core materials C1 and C2, they may be the same material or different materials. For instance, core material C1 may be a SAP-loaded nonwoven material, i.e. a smooth or textured nonwoven carrier with beads or particles of super absorbent polymer (SAP) loaded thereon, and the core C2 may be an ADL (acquisition distribution layer) material, but the reverse combination is equally possible. Embodiments are also envisaged wherein both the core materials C1 and C2 are made of a SAP-loaded nonwoven material, and embodiments wherein both the core materials C1 and C2 are made of an ADL material.

The machine is configured to feed each of the first core material C1, the second core material C2 and the carrier material CM (i.e. the first web material, the second web material, and the third web material) in a machine direction MD, which identifies the main extension direction of the machine 1, as well as the main process direction of the workflow in the machine 1. Other reference directions marked in FIG. 1 comprise a cross direction CD, which is transverse to the machine direction, and a direction ZM (essentially vertical) which is orthogonal to both the machine and the cross directions MD, CD.

The supply unit 6 is configured to route the carrier material CM through the machine 1 in the machine direction MD to meet the first processing unit 2 and the second processing unit 4. In this regard, the first processing unit 2 is arranged upstream of the second processing unit 4 in the machine direction MD.

With reference to FIGS. 1, 2 and 4, the first processing unit 2 comprises a first cutting device 8. The cutting device 8 comprises a pair of counter rotating rollers 8U and 8L (upper and lower) having an axis of rotation parallel to the cross direction CD.

The cutting device 8 is configured for cutting the first core material C1 into a first pattern P1 comprising pairs of oppositely tapering figures F1, F2. The feature "oppositely tapering" is intended to designate a condition whereby the first figure tapers (i.e. narrows in dimension) along a given direction and in a given orientation of the same direction, and the second figure tapers (i.e. narrows in dimension) along the same given direction but in the opposite orientation. For instance, in embodiments of the invention the oppositely tapering figures F1, F2 taper in the cross direction CD, but figure F1 tapers right to left (with reference to the machine direction MD), while figure F2 tapers left to right.

More in detail, each pair of oppositely tapering figures F1 and F2 comprises a first tapering figure F1 and a second tapering figure F2 that are adjacent in the machine direction MD and staggered in the cross direction CD by a distance CD1.

FIGS. 2 and 4, as well as the enlarged details of FIGS. 3 and 5, show alternative embodiments of the tapering figures that can be used according to the invention. The reference numbers and letters are intentionally not changed across the embodiments as they actually designate comparable features.

In the embodiments of FIGS. 2-3 each pair of oppositely tapering figures F1, F2 is a triangular figure comprising a base B1, B2 respectively (bases B1, B2 coincide with the sides of the parallelogram outline) and a vertex V1, V2, respectively, opposite to the base B1, B2, whereby each vertex V1, V2 has a staggered location in the cross direction with respect to the base B2, B1 the other figure in the pair. Preferably (as shown in the figures), each triangular figure F1, F2 is an isosceles triangle. In some embodiments, the triangular figure whether an isosceles triangle or not—may comprise rounded vertices.

In other words, the two triangular figures are staggered in the cross direction as if they had been "slid" along a pair of adjacent sides other than the bases, whereby sides T1 and T2 of the overall staggered figure corresponding to the pattern P1—which correspond to a side T1 from figure F1 and a side T2 from figure F2—are also staggered in the cross direction CD, while the bases B1, B2 are parallel to the machine direction MD and parallel to one another.

Each of the oppositely tapering figures F1, F2 FIG. 2 also clearly shows the opposite tapering of figures F1, F2: vertex V1 faces left of the machine direction, hence the tapering of figure F1 goes from right to left, while vertex V2 faces right of the machine direction, hence the tapering of figure F2 goes from left to right.

In the embodiments of FIGS. 4-5 each pair of oppositely tapering figures F1, F2 is a trapezoid figure comprising a first (major) base B1A, B2A and a second (minor) base B1B, B2B opposite and parallel to the first base B1A, B2A, whereby each second base B1B, B2B is located staggered in the cross direction with respect to the first base B1A, B2A of the other figure in the pair. Preferably (as shown in the figures), each trapezoid figure F1, F2 is an isosceles trapezium. In some embodiments, the trapezoid figure—whether an isosceles trapezium or not—may comprise rounded vertices.

In other words, the two trapezoid figures F1, F2 are staggered in the cross direction CD as if they had been "slid" along a pair of adjacent sides other than the bases, whereby sides T1 and T2 of the overall staggered figure corresponding to the pattern P1—which correspond to a side T1 from figure F1 and a side T2 from figure F2—are also staggered in the cross direction CD, while the bases B1A, B2B and B1B, B2A are parallel to the machine direction MD and parallel to one another.

FIG. 4 also clearly shows the opposite tapering of figures F1, F2: base B1B faces left of the machine direction, hence the tapering of figure F1 goes from right to left, while base B2B faces right of the machine direction, hence the tapering of figure F2 goes from left to right.

The first processing unit further comprises a first spacer device 10 configured for spacing the first tapering figure F1 from the second tapering figure F2 in the machine direction MD, and—in preferred embodiments such as shown in the figures herein—also configured to operate as a laydown device for laying the first tapering figure F1 and the second tapering figure F2 spaced in the machine direction MD and staggered in the cross direction CD onto the carrier material CM.

The first spacer device 10 comprises a first rotary re-pitching device including a respective hub having an axis of rotation CD10 parallel to the cross direction CD and spacer members movably mounted on the first hub and displaceable in a rotary motion around the first axis of rotation relative to the first hub. Accordingly, while the hub of the spacer device 10 is set in rotation according to the processing speed of the machine 1, the spacer members may move circumferentially along an outer guide surface or feature of the hub (the axis CD10 being the axis of rotation of the spacer members) independently of the base rotational movement of the hub to vary the spacing of the figures F1, F2 in the machine direction MD. In this sense, the space members—in a way per se known—are configured to engage the figures F1, F2 to displace the same in the machine direction, thereby achieving the spacing thereof in the machine direction MD As anticipated, the first spacer 10 here operates also as a laydown device of the rotary transfer type. The spacer device 10 is accordingly configured to lay the first tapering figure and the second tapering figure F1, F2 spaced in the machine direction MD (by the spacer device 10 itself) and staggered in the cross direction CD and transferring the same onto the carrier material CM. In other embodiments, however, a (first) laydown device—for instance of the rotary transfer type—may be provided separate from the spacer device 10, whereby in such embodiments the spacer device 10 relays the machine direction spaced, cross direction staggered figures F1, F2 to the first laydown device. More in detail, in such embodiments the laydown device may be positioned downstream of the spacer 10 and may comprises a rotary transfer device having an axis of rotation parallel to the cross direction CD and configured to receive the first tapering figure (F1) and the second tapering figure (F2) spaced in the machine direction (MD) and staggered in the cross direction (CD).

The second processing unit will now be described. In preferred embodiments the second processing unit is essentially identical to the processing unit 2, but a full description will be provided herein anyway, as there are some unit-specific information that hold a relevance for the disclosure.

With reference again to FIGS. 1, 2 and 4, the second processing unit 4 comprises a second cutting device 16. The cutting device 16 comprises a pair of counter rotating rollers 16U and 16L (upper and lower) having an axis of rotation parallel to the cross direction CD.

The cutting device 16 is configured for cutting the second core material into a second pattern P2 comprising pairs of oppositely tapering figures F3, F4. As with the foregoing disclosure, the feature "oppositely tapering" is intended to designate a condition whereby the first figure tapers (i.e. narrows in dimension) along a given direction and in a given orientation of the same direction, and the second figure tapers (i.e. narrows in dimension) along the same given direction but in the opposite orientation. For instance, in embodiments of the invention the oppositely tapering figures F3, F4 taper in the cross direction CD, but figure F3 tapers left to right (with reference to the machine direction MD), while figure F4 tapers right to left. In this sense, figures F3 and F4 have a reverse tapering with respect to the pair comprising the first tapering figure F1 and the second tapering figure F2.

More in detail, each pair of oppositely tapering figures F3 and F4 comprises—just like the pair in the pattern 1—a first tapering figure F2 and a second tapering figure F4 that are adjacent in the machine direction MD and staggered in the cross direction CD by a distance CD2.

FIGS. 2 and 4, as well as the enlarged details of FIGS. 3 and 5, show alternative embodiments of the tapering figures that can be used according to the invention. The reference numbers and letters are intentionally not changed across the embodiments as they actually designate comparable features.

In the embodiments of FIGS. 2-3 each pair of oppositely tapering figures F3, F4 is a triangular figure comprising a base B3, B4 respectively and a vertex V3, V4, respectively, opposite to the base B3, B4, whereby each vertex V3, V4 has a staggered location in the cross direction with respect to the base B4, B3 the other figure in the pair.

Preferably (as shown in the figures), each triangular figure F3, F4 is an isosceles triangle. In some embodiments, the triangular figure—whether an isosceles triangle or not—may comprise rounded vertices.

In other words, the two triangular figures are staggered in the cross direction as if they had been "slid" along a pair of adjacent sides other than the bases, whereby sides T3 and T4 of the overall staggered figure corresponding to the pattern P2—which correspond to a side T3 from figure F3 and a side T4 from figure F4—are also staggered in the cross direction CD, while the bases B3, B4 are parallel to the machine direction MD and parallel to one another.

FIG. 2 also clearly shows the opposite tapering of figures F3, F4: vertex V3 faces left of the machine direction, hence the tapering of figure F3 goes from right to left, while vertex V4 faces right of the machine direction, hence the tapering of figure F4 goes from left to right.

In the embodiments of FIGS. 4-5 each pair of oppositely tapering figures F3, F4 is a trapezoid figure comprising a first (major) base B3A, B4A and a second (minor) base B3B, B4B opposite and parallel to the first base B3A, B4A, whereby each second base B3B, B4B is located staggered in the cross direction with respect to the first base B3A, B4A of the other figure in the pair. Preferably (as shown in the figures), each trapezoid figure F3, F4 is an isosceles trapezium. In some embodiments, the trapezoid figure—whether an isosceles trapezium or not—may comprise rounded vertices.

In other words, the two trapezoid figures F3, F4 are staggered in the cross direction CD as if they had been "slid" along a pair of adjacent sides other than the bases, whereby sides T3 and T4 of the overall staggered figure corresponding to the pattern P2—which correspond to a side T3 from figure F4 and a side T4 from figure F4—are also staggered in the cross direction CD, while the bases B3A, B4B and B3B, B4A are parallel to the machine direction MD and parallel to one another.

FIG. 4 also clearly shows the opposite tapering of figures F3, F4: base B3B faces left of the machine direction, hence the tapering of figure F3 goes from right to left, while base B4B faces right of the machine direction, hence the tapering of figure F4 goes from left to right.

The second processing unit 4 further comprises a second spacer device 18 configured for spacing the third tapering figure F3 from the fourth tapering figure F4 in the machine direction MD and—in preferred embodiments such as shown in the figures herein—also configured to operate as a laydown device for laying the laying the third tapering figure F3 and the second tapering figure F4 spaced in the machine direction MD and staggered in the cross direction CD onto the carrier material CM to overlap a portion of the third tapering figure F3 with a portion of the first tapering figure F1 into a first hourglass shape H1, and a portion of the fourth tapering figure F4 with a portion of the first tapering figure F1 into a second hourglass shape H2.

The second spacer device 18 comprises a rotary re-pitching device including a respective hub having a fourth axis of rotation CD18 parallel to the cross direction CD and spacer members movably mounted on the hub and displaceable in a rotary motion around the third axis of rotation CD18 relative to the hub. Accordingly, while the hub of the spacer device 18 is set in rotation according to the processing speed of the machine 1, the spacer members may move circumferentially along an outer guide surface or feature of the hub (the axis CD18 being the axis of rotation of the spacer members) independently of the base rotational movement of the hub to vary the spacing of the figures F3, F4 in the machine direction MD. In this sense, the spacer members—in a way per se known—are configured to engage the figures F3, F4 to displace the same in the machine direction, thereby achieving the spacing thereof in the machine direction MD As anticipated, the second spacer device 18—similarly to the spacer device 10—here operates also as a laydown device of the rotary transfer type. The spacer device 18 is accordingly configured to lay the third tapering figure F3 and the fourth tapering figure F4 spaced in the machine direction MD (by the spacer device 18 itself) and staggered in the cross direction CD and transferring the same onto the carrier material CM to eventually define the hourglass shaped figures H1, H2. In other embodiments, however, a (second) laydown device—for instance of the rotary transfer type—may be provided separate from the spacer device 18, whereby in such embodiments the spacer device 18 relays the machine direction spaced, cross direction staggered figures F3, F4 to the second laydown device. More in detail, in such embodiments the laydown device may be positioned downstream of the spacer 18 and may comprises a rotary transfer device having an axis of rotation parallel to the cross direction CD and configured to receive the third tapering figure (F3) and the fourth tapering figure (F4) spaced in the machine direction (MD) and staggered in the cross direction (CD) and transferring the same onto the carrier material CM to eventually define the hourglass shaped figures H1, H2.

In preferred embodiments, the machine 1 comprises an embossing unit 24 configured to provide an embossed pattern on the first hourglass shape H1 and the second hourglass shape H2. The pairs of figures F1, F3 and F2 and F4 laid onto the carrier material CM and overlapping into the hourglass shapes H1, H2 correspond to the absorbent cores of sanitary products manufactured by the machine 1, whereby the embossment is provided on the to-be cores, for instance to provide fluid drain channels.

In some embodiments, with reference to FIG. 1A, the machine 1 may comprise a supply unit 26 for a backing material BM, wherein the backing material BM comprises a fourth web material. Reference C in FIGS. 1, 1A indicates the connection point of the section in FIG. 1A with the rest of the machine 1. and wherein the supply unit 26 is configured to lay the backing material BM onto the first hourglass shape H1 and the second hourglass shape H2 made of the first and second core materials (as they both are made of figures from patterns P1, P2) to enclose the first hourglass shape H1 and the second hourglass shape H2 together with the carrier material CM, thereby defining a layered arrangement of a sanitary product: top sheet (carrier material CM, absorbent core (figure H1 or H2), back sheet (backing material BM). Downstream of the supply unit 26, a bonding unit 28 (for instance a thermal or ultrasonic welding machine) is provided for bonding the materials CM and BM with a pattern which depends on the final shape and design of the products, and downstream of the bonding unit 28 a cutting unit 30 is provided that cuts the sanitary products into the final shape thereof. Purely by way of example, both the bonding unit 28 and the cutting unit 30 comprise a pair of counter rotating bonding or cutting rollers, respectively. Alternatively, the bonding unit 28 may comprise an anvil-horn pair to provide an ultrasonic bonding.

Operation of the machine 1—and with it the method of manufacturing sanitary products according to the invention will now be described. Reference shall be made to all of the figures as they illustrate the machine in its entirety (FIG. 1) as well as the output of each station (FIGS. 2-5).

As to FIGS. 2 and 4, they show subsequent processing stages taking place across the machine 1, and each stage within FIGS. 2 and 4 is associated to a reference i), ii), iii), iv), v) which is identically reproduced in FIG. 1 to remark the correspondence between each stage and the element of the machine 1 it happens at.

According to the invention, manufacturing of sanitary products such as panty liners, or light-inco diapers (although the range is not limited to the latter) though the machine 1 includes providing the first core material C1, which comprises the first web material, providing the second core material C2, which comprises the second web material, and providing the carrier material CM, which comprises the third web material, and feeding each of the core material C1, core material C2 and carrier material CM in the machine direction MD. Providing each material as a web material allows automatic processing within the machine 1, as it is common in the field.

The carrier material CM is essentially fed through the machine 1, i.e. it goes through the machine 1 along the machine direction to meet with the output of the first processing station 2 and the second processing station 4.

Cutting of the first core material C1 into the pattern P1 (stage i)) comprising pairs of oppositely tapering figures F1, F2 is done at the processing station 2 by means of the cutting device 8. The core material C1 is fed between the cutting rollers 8U and 8L and comes out cut into patterns P1. Patterns P1 can be cut seamlessly and continuously, and a very little amount of scrap—which is negligible in terms of costs and disposal obligations—is generated at the cutout areas where staggering between the figures occurs.

Once cut by the rollers 8U and 8L, the web of the core material C1 moves on and winds onto the spacer device 10 (stage ii)). Here, the spacer members on the hub of the spacer device 10 engage a corresponding one of figure F1 and F2 and move circumferentially to provide spacing of the first tapering figure F1 from the second tapering figure F2 in the machine direction MD by a distance MD1.

The machine direction spaced and cross direction staggered figures F1 and F2 are further laid down onto the carrier material CM by the spacer device 10, which provides the laying of the first tapering figure F1 and the second tapering figure F2 spaced in the machine direction MD and staggered in the cross direction CD onto the carrier material CM which in the routing thereof through the machine 1 meets the station 2 to receive the figures F1 and F2.

Cutting of the second core material C2 into the pattern P2 (stage iii)) comprising pairs of oppositely tapering figures F3, F4 is done at the processing station 4 by means of the cutting device 16. While still oppositely tapering as the figures F1 and F2, cutting is made so to provide the figures F3 and F4 with a reverse opposite tapering as compared to that of figures F1 and F2. The core material C2 is fed between the cutting rollers 16U and 16L and comes out cut into patterns P2. As with the patterns P1, the patterns P2 can be cut seamlessly and continuously, and a very little amount of scrap—which is negligible in terms of costs and disposal obligations—is generated at the cutout areas where staggering between the figures occurs.

Once cut by the rollers 16U and 16L, the web of the core material C2 moves on and winds onto the spacer device (stage iii)). Here, the spacer members on the hub of the spacer device 18 engage a corresponding one of figure F3 and F4 and move circumferentially to provide spacing of the first tapering figure F3 from the second tapering figure F4 in the machine direction by a distance MD2. When figures F1 and F2 are identical in size and shape to figures F3 and F4, like in the preferred embodiments, distance MD2 is preferably identical to distance MD1. Likewise, when figures F1 and F2 are identical in size and shape to figures F3 and F4 the staggering distances CD1 and CD2 are identical, i.e. the patterns P1, P2 are identical and pre-cut with identical cross direction staggering CD1, CD2.

The machine direction spaced and cross direction staggered figures F3 and F4 are further laid down onto the carrier material CM by the spacer device 10, which provides the laying of the first tapering figure F3 and the second tapering figure F4 spaced in the machine direction MD and staggered in the cross direction CD onto the carrier material CM which in the routing thereof through the machine 1 meets the station 4 to receive the figures F3 and F4.

Laying of the figures F3, F4 spaced in the machine direction MD and staggered in the cross direction CD onto the carrier material CM is provided so as to overlap a portion of the third tapering figure F3 with a portion of the first tapering figure F1 into the first hourglass shape H1, and a portion of the fourth tapering figure F4 with a portion of the first tapering figure F2 into a second hourglass shape H2. Because the figures F3 and F4 are laid onto the carrier material CM after the figures F1 and F2, in the embodiment illustrated herein the hourglass shapes H1 and H2 feature figures F3 and F4 on top of figures F1 and F2 anyway. FIGS. 3 and 5 show the overlapping portions OV13 (F1, F3) and OV24 (F2, F4): diamond shaped for the triangular figures (FIG. 3), and hexagonal shaped for the trapezoid figures (FIG. 5).

The newly formed absorbent cores having the hourglass shapes H1 and H2 are then embossed with a desired pattern—for instance to provide a texture or fluid collection/draining channels, or else a central embossment at the overlapping portions between figures F1, F3 and F2, F4—by the embossing unit 24 (stage ix), FIG. 1).

The last processing stage through the machine 1 (or downstream of the machine 1 if the relevant equipment is not onboard the machine 1 itself) may comprise supplying of the backing material BM through the supply unit 26 to enclose the cores formed of figures F1, F3 and F2, F4 into a top sheet provided by the carrier material CM and a back sheet provided by the backing material BM. The sanitary products are then bonded and cut to shape by the bonding unit 28 and the cutting unit 30.

Accordingly, sanitary products are manufactured according to the invention wherein the high-grade core materials C1 and C2 are processed with extremely low waste and with very high process rate thanks to the patterns P1 and P2 being used as a precursor of the hourglass shape as they are assembled into the required hourglass shapes through the machine 1. The only additional scrap or waste may concern the backing and the carrier materials BM, CM, which are however lower grade materials than the core materials, especially when the latter comprise SAP or ADL.

Note also that in embodiments of the invention the hourglass shapes H1 and H2, which each provide the absorbent core of a sanitary product, may be defined by tapering figures different from one another. For instance, the hourglass shapes H1, H2 may be defined by overlapping triangular tapering figures F1, F2 with trapezoid shaped tapering figures F3, F4. The sole arrangement required for the machine 1 would concern the provision of cutting rollers 8U, 8L configured for cutting a first pattern P1 of the type depicted in FIGS. 3, 4—i.e. featuring oppositely tapering figures F1, F2 each being a triangular figure comprising a base B1, B2 respectively (bases B1, B2 coincide with the sides of the parallelogram outline) and a vertex V1, V2, respectively, opposite to the base B1, B2, whereby each vertex V1, V2 has a staggered location in the cross direction with respect to the base B2, B1 the other figure in the pair—and the provision of cutting rollers 16U, 16L configured for cutting a second pattern P2 of the type depicted in FIG. 4, 5—i.e. with two trapezoid figures comprising a first (major) base B3A, B4A and a second (minor) base B3B, B4B opposite and parallel to the first base B3A, B4A, whereby each second base B3B, B4B is located staggered in the cross direction with respect to the first base B3A, B4A of the other figure in the pair. Of course, the reverse arrangement is possible as well: figure F1, F2 cut according to FIGS. 4, 5 and figures F3, F4 cut according to FIGS. 2 and 3. Rollers 8U, 8L and 16U, 16L would be arranged accordingly.

A preferred positioning of different tapering figures (triangular-trapezoid) when assembling the hourglass shapes H1, H2 may comprise creating an overlap such that the vertices at the minor base of the trapezoid figure each lie on a side of the triangular figure other than the base. With triangular figures provided as isosceles triangles and trapezoid figures provided as isosceles trapezii the tapering rate of each figure and the geometrical height (i.e. the vertex to base distance for the triangle, and the base to base distance for the trapezium) may be adjusted to provide hourglass shaped figures with a variety of aspect ratios.

Naturally, while the principle of the invention remains the same, the details of construction and the embodiments may widely vary with respect to what has been described and illustrated purely by way of example, without departing from the scope of the present invention.

The invention claimed is:

1. A method for manufacturing sanitary products, comprising:
   providing a first core material comprising a first web material,
   providing a second core material comprising a second web material,
   providing a carrier material comprising a third web material,
   feeding each of the first core material, the second core material and the carrier material in a machine direction,
   cutting the first core material into a first pattern comprising first pairs of oppositely tapering figures, each first pair of oppositely tapering figures comprising a first tapering figure and a second tapering figure adjacent in the machine direction and staggered in a cross direction transverse to the machine direction,
   spacing the first tapering figure from the second tapering figure in the machine direction,
   laying the first tapering figure and the second tapering figure spaced in the machine direction and staggered in the cross direction onto the carrier material,
   cutting the second core material into a second pattern comprising second pairs of oppositely tapering figures, each second pair of oppositely tapering figures comprising a third tapering figure and a fourth tapering figure adjacent in the machine direction and staggered in the cross direction, the third tapering figure and the fourth tapering figure having a reverse tapering with respect to the first tapering figure and the second tapering figure, respectively,
   spacing the third tapering figure from the fourth tapering figure in the machine direction,
   laying the third tapering figure and the fourth tapering figure spaced in the machine direction and staggered in the cross direction onto the carrier material to overlap a portion of the third tapering figure with a portion of the first tapering figure into a first hourglass shape, and a portion of the fourth tapering figure with a portion of the second tapering figure into a second hourglass shape.

2. The method of claim 1, wherein the first tapering figure and the second tapering figure taper along the cross direction.

3. The method of claim 1, wherein the third tapering figure and the fourth tapering figure taper along the cross direction.

4. The method of claim 1, wherein each figure of the first and second pairs of oppositely tapering figures is a triangular figure comprising a base and a vertex opposite to said base, whereby each vertex has a staggered location in the cross direction with respect to the base of the other figure in the respective first and second pairs.

5. The method of claim 1, wherein each figure of the first and second pairs of oppositely tapering figures is a trapezoid figure comprising a first base and a second base opposite and parallel to said first base, whereby each second base has a staggered location in the cross direction with respect to the first base of the other figure in the respective first and second pairs.

6. A machine for manufacturing sanitary products, comprising:
   a first processing unit for a first core material, the first core material comprising a first web material, a second processing unit for a second core material, the second core material comprising a second web material, a supply unit for a carrier material, the carrier material comprising a third web material, wherein the machine is configured to feed each of the first core material, the second core material and the carrier material in a machine direction, wherein the supply unit is configured to route the carrier material through the machine in the machine direction to meet the first processing unit and the second processing unit, wherein the first processing unit comprises:

a first cutting device for cutting the first core material into a first pattern comprising first pairs of oppositely tapering figures, each first pair of oppositely tapering figures of the first pattern comprising a first tapering figure and a second tapering figure adjacent in the machine direction and staggered in a cross direction transverse to the machine direction, a first spacer device configured for spacing the first tapering figure from the second tapering figure in the machine direction, a first laydown device configured for laying the first tapering figure and the second tapering figure staggered in the cross direction and spaced in the machine direction onto the carrier material, wherein the second processing unit comprises:

a second cutting device configured for cutting the second core material into a second pattern comprising second pairs of oppositely tapering figures of the second pattern, each second pair of oppositely tapering figures comprising a third tapering figure and a fourth tapering figure adjacent in the machine direction and staggered in the cross direction transverse to the machine direction, the third tapering figure and the fourth tapering figure having a reverse tapering with respect to the first tapering figure and the second tapering figure, respectively, a second spacer device configured for spacing the third tapering figure from the fourth tapering figure in the machine direction, a second laydown device configured for laying the third tapering figure and the fourth tapering figure staggered in the cross direction and spaced in the machine direction onto the carrier material to overlap a portion of the third tapering figure with a portion of the first tapering figure into a first hourglass shape, and a portion of the fourth tapering figure with a portion of the second tapering figure into a second hourglass shape.

7. The machine according to claim 6, wherein the first processing unit is arranged upstream of the second processing unit in the machine direction.

8. The machine according to claim 6, wherein the first spacer device and the second spacer device each comprise a first rotary re-pitching device, the first rotary re-pitching device comprising a hub having an axis of rotation parallel to the cross direction and spacer members movably mounted on the hub and displaceable in a rotary motion around the axis of rotation relative to the hub, the spacer members of the first spacer device and the third second spacer device being configured to engage a corresponding one of the first tapering figure and the second tapering figure, and the third tapering figure and the fourth tapering figure, respectively, to provide spacing thereof in the machine direction.

9. The machine of claim 6, wherein:

said first spacer device also provides said first laydown device, whereby said first spacer device is also configured for laying the first tapering figure and the second tapering figure staggered in the cross direction and spaced in the machine direction onto the carrier material, and said second spacer device also provides said second laydown device, whereby said second spacer device is configured for laying the third tapering figure and the fourth tapering figure staggered in the cross direction (CD) and spaced in the machine direction onto the carrier material to overlap the portion of the third tapering figure with the portion of the first tapering figure into the first hourglass shape, and the portion of the fourth tapering figure with the portion of the second tapering figure into the second hourglass shape.

10. The machine of claim 6, wherein the first laydown device and the second laydown device each comprise a rotary transfer device having an axis of rotation parallel to the cross direction and configured to receive, respectively, the first tapering figure and the second tapering figure spaced in the machine direction and staggered in the cross direction, and the third tapering figure and the fourth tapering figure spaced in the machine direction and staggered in the cross direction and transferring the same onto the carrier material.

11. The machine of claim 6, further comprising an embossing unit configured to provide an embossed pattern on the first hourglass shape and the second hourglass shape.

12. The machine of claim 6, further comprising a supply unit for a backing material, the backing material comprising a fourth web material, wherein the supply unit for the backing material is configured to lay the backing material onto the first hourglass shape and the second hourglass shape made of the first and second core materials to enclose the first hourglass shape and the second hourglass shape together with the carrier material.

* * * * *